United States Patent [19]

Wang et al.

[11] Patent Number: 5,316,704
[45] Date of Patent: May 31, 1994

[54] PROCESS FOR FABRICATING FULL SIZED EXPANSILE HYDROGEL INTRAOCULAR LENSES

[75] Inventors: Yading Wang, Arcadia; Stephen O. Zhou, Hacienda Heights; Thomas P. Richards, Los Angeles, all of Calif.

[73] Assignee: Kabi Pharmacia Ophthalmics Inc., Monrovia, Calif.

[21] Appl. No.: 951,775

[22] Filed: Sep. 28, 1992

[51] Int. Cl.⁵ .............................................. B29D 11/00
[52] U.S. Cl. ...................... 264/2.6; 264/1.7; 264/2.7
[58] Field of Search ........................... 264/1.7, 2.6, 2.7

[56] References Cited

U.S. PATENT DOCUMENTS

| | | | |
|---|---|---|---|
| 3,361,858 | 1/1968 | Wichterle | 264/2.6 |
| 4,573,998 | 3/1986 | Mazzocco | 623/6 |
| 4,731,079 | 3/1988 | Stoy | 623/6 |
| 4,743,254 | 5/1988 | Davenport | 623/6 |
| 4,808,182 | 2/1989 | Barrett | 623/6 |
| 4,813,954 | 3/1989 | Siepser | 623/6 |
| 4,833,890 | 5/1989 | Kelman | 623/6 |
| 4,911,714 | 3/1990 | Poley | 623/6 |
| 4,919,662 | 4/1990 | Knoll et al. | 623/6 |
| 4,936,850 | 6/1990 | Barrett | 623/6 |
| 4,993,936 | 2/1991 | Siepser | 425/408 |
| 4,997,442 | 3/1991 | Barret | 623/6 |
| 5,147,394 | 9/1992 | Siepser et al. | 623/6 |
| 5,217,491 | 6/1993 | Vanderbilt | 264/1.7 |

FOREIGN PATENT DOCUMENTS

| | | | |
|---|---|---|---|
| 3940891 | 6/1991 | Fed. Rep. of Germany | A61L 27/00 |
| 87281928 | 2/1986 | Japan | C03B 11/00 |
| 839522 | 6/1981 | U.S.S.R. | A61F 1/16 |
| 2114578 | 6/1980 | United Kingdom | C08F 220/55 |

OTHER PUBLICATIONS

Dreifus, et al., "Intracameral Lenses Made of Hydrocolloidal Acrylates", Ceskoslovenska oftalmologie, vol. 16, No. 2, p. 1860.

Packard, et al., "Poly-HEMA as a material for intraocular lens implantation: a preliminary report", British Journal of Ophthalmoolgy, 1981, 65, 585-587.

*Primary Examiner*—James Lowe
*Attorney, Agent, or Firm*—Poms, Smith, Lande & Rose

[57] ABSTRACT

Expansile hydrogel intraocular lenses are heated above their elastic deformation temperatures and deformed into an elongated configuration having at least one reduced dimension suitable for insertion through a small surgical incision. The lenses are allowed to cool in this configuration and retain the deformed shape prior to surgical implantation. Following implantation the lenses hydrate into an enlarged elastic form reassuming the original lens configuration of full capsule size.

15 Claims, 4 Drawing Sheets

PROCESS FOR FABRICATING FULL SIZED EXPANSILE HYDROGEL INTRAOCULAR LENSES

BACKGROUND OF THE INVENTION

1. Field of the Invention

The present invention relates generally to intraocular lenses suitable for implantation using small incision surgical techniques. More particularly, the present invention involves hydrogel intraocular lenses and methods for their deformation in a dehydrated state to a size which is sufficiently reduced for their small incision implantation following cataract surgery. Subsequent to surgical implantation, the deformed lenses hydrate within the ocular environment to full sized lenses.

2. Description of Related Art

Since the early 1940's optical devices in the form of intraocular lenses have been utilized to replace the natural physiological crystalline ocular lens in humans and other mammals. Typically, the intraocular lens is implanted within the ocular environment immediately after surgically removing the natural lens which has become opaque or otherwise damaged by cataract formation or injury. For decades the most prevalently utilized materials for forming intraocular lenses were acrylates or methacrylates and particularly polymethylmethacrylate, a rigid, glassy polymer.

More recently developed surgical techniques and improved instrumentation have made it possible to remove the opaque or damaged natural lens through incision sizes as small as 2–3 mm. This contrasts sharply with earlier methods which involved forming incisions up to 9 or 10 mm in length in order to remove the natural lens and insert the intraocular lens. Because small incision surgery is much less traumatic for patients and decreases complications and healing time, this technique has become the method of choice for a large number of ophthalmic surgeons.

Since full-size intraocular lenses have diameters in the range of 8–13 mm, far exceeding the 2–3 mm incision size, the standard rigid polymethylmethacrylate lenses are not suitable for direct implantation through the reduced incision sizes. Thus, a number of different intraocular lens designs and materials have been developed for use in connection with small incision surgical techniques. One approach utilizes the concept of preparing lenses from elastomeric materials such as silicones and thermoplastic polymers Prior to surgically inserting the elastomeric lens, the surgeon rolls or folds the lens so that it is reduced in size for passing into the eye through a smaller incision. Once placed within the eye, the lens unfolds or unrolls to its full size.

One problem associated with these elastomeric lenses is the possibility that permanent deformation or crease marks may occur when the lens is folded or rolled. This is especially a concern at the center of the lens optical zone where most of the rolling or folding deformation take place.

Another approach to providing a small incision intraocular lens is suggested in U.S. Pat. No. 4,731,079. This reference discloses an intraocular lens formed of a polymer having a softening (or glass transition) temperature less than 42° C. and preferably about body temperature. The lens can be heated to above its softening temperature and deformed by compression or elongation to reduce at least one dimension. Then, by cooling the lens at a temperature substantially below its softening temperature, the lens will remain in the deformed configuration until it is warmed. Ophthalmic surgeons can implant the deformed lens and once the lens warms to body temperature it returns to its original configuration.

A major problem associated with these intraocular lenses is the restricted number of polymers available for preparing the lenses. Polymethylmethacrylate has a glass transition temperature above 100° C. and thus cannot be used to form these lenses. Most acrylates and methacrylates have similarly high glass transition temperatures. Through formulating the lenses with plasticizers will lower the glass transition temperature, the presence of plasticizers in intraocular lenses is generally unacceptable to most surgeons because of potential leaching problems. Alternatively, water is a suitable plasticizer, however, only small amounts of water, typically less than 10%, can be utilized in the polymers to place the glass transition in the appropriate range. Thus, typical hydrogels which have much higher amounts of water are not suitable for fabricating the deformable lenses.

An additional drawback with this suggested small incision intraocular lens is the added degree of surgical complexity required to deform the lens into its small incision configuration. The lenses are disclosed in U.S. Pat. No. 4,731,079 as being packaged in a form that requires the implanting surgeon to warm, deform, and cool the lens immediately prior to its implantation. This procedure is considerably more involved than traditional lens implantation techniques.

Another suggested approach for small incision lens implantation involves implanting hydrogel intraocular lenses in their smaller dehydrated state. Once the implanted dehydrated lens is secured within the eye it reportedly hydrates and swells in the aqueous ocular environment. A significant problem associated with this approach is the large amount of swelling required to produce an effective lens diameter. In order to fully swell the lens from a diameter of about 3 mm to about 6 mm the lens must swell 8 times by volume. This translates to a lens which is 85% water. For larger full sized intraocular lenses the swell volume is much higher. Since most hydrogels are structurally very weak at these high water contents, many surgeons are reluctant to implant them. Also, these high water content hydrogels have very low refractive indices of around 1.36 and in order to achieve suitable refractive powers the hydrogel lens must be thicker in the optic portion. As a result, a dehydrated hydrogel intraocular lens that will fit through a desirably small incision will not swell to a sufficiently large hydrated size to effectively function as an intraocular lens. This problem is compounded if larger, full size intraocular lenses are desired that have optic diameters greater than 6 mm. Alternatively, in order to produce a hydrated lens having a sufficient optic diameter the dehydrated hydrogel lens must be larger than desirable for a small incision implantation procedure.

Alternatively, U.S. Pat. No, 4,919,662 suggests rolling or folding hydrogel intraocular lenses in their elastic hydrated form, and then dehydrating the lenses at lower temperatures to fix the rolled or folded lens configuration at a size suitable for small incision implantation. Once implanted, these lenses hydrate and swell to the original lens configuration. Unfortunately, this method has the disadvantage of requiring the handling of fully hydrated lenses during the deforming process. Unfortunately, hydrated lenses have relatively weak tear strengths and handling the lenses causes frequent tearing damage.

U.S. Pat. No. 4,813,954 discloses expansile hydrogel intraocular lenses which are formed by simultaneously deforming and dehydrating hydrogel intraocular lenses prior to implanting the lenses in their dehydrated state. Lenses subjected to this treatment swell to about 180% of their reduced size. For example, lenses deformed or compressed to a diameter of 3.2 mm will swell to only about 5.8 mm. Thus, while providing some advantages over simply implanting dehydrated lenses, the method and lenses described in U.S. Pat. No. 4,813,954 do not result in full sized implanted intraocular lenses of over 8 mm.

As those skilled in the art will appreciate, each of these prior art small incision lens approaches requires an intraocular lens having generally circular, radially extending flange-type haptics as opposed to traditional filament style haptics. This is because the hydrogel materials do not have sufficient strength to stabilize the lens optics when shaped in conventional filament haptic forms. Thus, it is desirable to utilize lenses having full sized optics with diameters greater than the traditional 6 mm known in the art in order to provide lenses that stably remain in position following implantation.

Accordingly, it is an object of the present invention to provide expansile hydrogel intraocular lenses suitable for small incision implantation.

It is an additional object of the present invention to provide full sized expansile hydrogel intraocular lenses and methods for their production.

It is further an object of the present invention to provide methods for fabricating small incision expansile hydrogel intraocular lenses which are suitable for packaging and storing in their reduced size.

SUMMARY OF THE INVENTION

The present invention accomplishes the above-mentioned objectives by providing methods for preparing expansile hydrogel intraocular lenses which, in their dehydrated form, are suitably sized for small incision implantation. Unlike many prior art expansile hydrogel intraocular lenses which, when dehydrated and suitably sized for small incision implantation, hydrate within the ocular environment to undesirably small lens sizes, the intraocular lenses of the present invention hydrate and swell to full sized intraocular lenses.

Generally speaking, the methods of the present invention involve deforming dehydrated hydrogel intraocular lenses under elevated temperatures and then freezing the deformed lenses in their dehydrated configuration. The lenses retain their deformed configuration until they are exposed to conditions under which the material becomes rubbery or elastic. These reformation conditions include exposing the lens to elevated temperatures or hydrating the lens material to form the hydrogel.

More particularly, the present invention provides methods for fabricating intraocular lenses suitably sized for small incision insertion by first providing a dehydrated intraocular lens having small dehydrated dimensions and formed of hydrogel forming polymer having an elastic deformation temperature, preferably above ambient or room temperature. The next step includes deforming the dehydrated intraocular lens at a temperature at least as high as the elastic deformation temperature to provide a deformed configuration with at least one of the dehydrated dimensions being sufficiently reduced to move the dehydrated and deformed lens through a small, typically 3 to 4 mm surgical incision. Finally, allowing the deformed and dehydrated intraocular lens to cool to a temperature sufficiently below the elastic deformation temperature freezes the deformed dehydrated intraocular lens in this small incision implantation deformed configuration.

Advantageously, once the lenses of the present invention are implanted within an aqueous physiological environment, the lenses hydrate and swell to effectively full sized lenses having diameters of over 6 to 8 mm or more. Following hydration the lenses also become elastic and acquire shape memory characteristics due to the elevated amount of water incorporated within the hydrogel material. This shape memory characteristic of the hydrated lenses makes it possible to perform the lens deformation processes using any of a variety of deformation techniques, including radial compression and tensile elongation without impacting the ability of the lenses to reform to their desired post-implantation configurations.

Exemplary hydrogel forming materials suitable for fabricating the expansile intraocular lenses of the present invention may be any polymer, copolymer, or polymer blend which is biocompatible and hydrates to a hydrogel having at least 20 wt % water content. Such materials include copolymers formed of at least one hydrophilic or water soluble monomer and one hydrophobic monomer. The relative amount of the various monomers used to produce the hydrogel forming materials will depend upon the desired final water content and the amount of material elasticity required to deform the lens above the desired elastic deformation temperature. The hydrogel materials also should have sufficient resiliency at their deformation temperatures to prevent permanent stretching or cracking during and after the deforming process, as known in the art.

Similarly, the shapes and dimensions of intraocular lenses suitable for deforming and implanting according to the present invention should be such that the lenses will withstand the physical deformation process and hydrate to effective post implantation configurations.

For example, full sized disc shaped lenses having bi-convex, plano-convex, or concavo-convex cross-sectional configurations and generally smooth, circular peripheral contact areas are suitable due to their generally symmetrical configuration. This configuration easily deforms to the desired small incision shape and hydrates to an appropriate full size lens configuration with minimal insertion and placement difficulty due to its symmetry. Similarly, disc shaped lenses having radially extending flange type haptics also may be utilized to practice the present invention. As those skilled in the art will appreciate, the outer periphery of the lens need not be continuous, as long as it is reasonably symmetrical and of sufficient physical dimension to provide a stable lens supporting structure. For ease of manufacturing, bi-convex full sized or radial flange haptic styles are preferred.

Further objects, features and advantages of the expansile hydrogel intraocular lenses of the present invention, as well as a better understanding thereof, will be afforded to those skilled in the art from a consideration of the following detailed explanation of exemplary embodiments when taken in connection with the following drawings.

DETAILED DESCRIPTION OF EXEMPLARY EMBODIMENTS

Figure 1A:
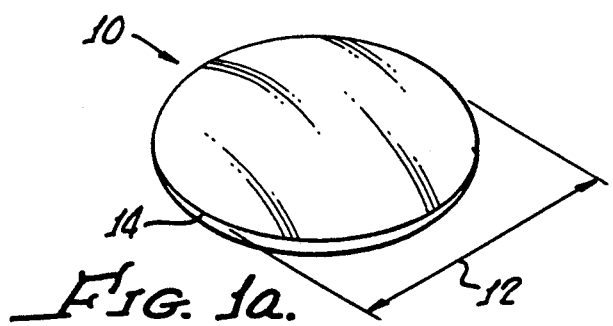
FIGS. 1a and b, respectively, illustrate an isometric view and an associated cross-sectional view of an exemplary small incision, full sized bi-convex, disc shape expansile hydrogel intraocular lens in its dehydrated form prior to deformation.

Broadly, the present invention provides methods for deforming or substantially reducing the size of shaped articles formed of polymer which is capable of subsequent swelling and expansile reformation in suitable fluids. These shaped polymeric articles can be deformed to a substantially reduced size while in the polymer's dry unswelled state known as its xerogel form. Then, once exposed to an appropriate fluid, the polymeric articles swell in all dimensions, returning to their original shape and a substantially increased size.

Because the methods of the present invention advantageously provide reduced sized deformed articles which swell to larger reformed volumes, they are particularly useful for preparing expansile intraocular lenses for implanting within the eye using small incision surgical techniques. The advantageously high swelling ratios allow the lenses to be configured for small incision insertion into the eye where the lenses hydrate and swell to full sized hydrogel intraocular lenses. Those skilled in the art will appreciate; however, that the methods of the present invention are suitable for other uses where polymeric articles capable of swelling to larger dimensions have utility.

The present invention is based upon the discovery that the hydrated elastic properties and shape memory properties of polymers which swell in the presence of fluids can be utilized to prepare deformable polymeric articles having specific, reduced dimensions yet which provide large swell volumes and shape reformation characteristics. That is the present invention involves exposing a hydrogel article in its dehydrated state to thermal conditions under which the dehydrated article is elastic, and then deforming and freezing the article in its deformed configuration. The result is a dehydrated and deformed polymeric article, which, following hydration, displays substantially increased swell volumes and dimensions.

More particularly, an exemplary embodiment of the present invention provides methods for fabricating intraocular lenses suitably sized for small incision insertion by first providing a dehydrated intraocular lens having at least one desirably small dehydrated dimension and formed of hydrogel forming polymer having an elastic deformation temperature. Preferably, the elastic deformation temperature is sufficiently high to be above ambient or room temperature. The next step includes deforming the dehydrated intraocular lens at a temperature at least as high as the elastic deformation temperature to provide a deformed configuration with at least one of the dehydrated dimensions being sufficiently reduced to move the dehydrated and deformed lens through a 3 to 4 mm surgical incision. Finally, allowing the dehydrated and deformed intraocular lens to cool to a temperature sufficiently below the elastic deformation temperature freezes the deformed dehydrated intraocular lens in its deformed configuration. The resulting expansile small incision intraocular lens is capable of swelling to a full sized hydrogel intraocular lens upon exposure to an aqueous environment such as an ocular physiological environment; yet, in its deformed state the intraocular lens has beneficially small dimensions suitable for contemporary small incision implantation techniques.

In accordance with the processes of the present invention, deforming the dehydrated intraocular lenses can be accomplished by any method which reduces the profile of the lens in at least one dimension. For example, a dehydrated lens can be compressed by applying pressure from its outer circumference inward. Vise clamps fitted with circular shaped fixtures can be utilized for this purpose. This method results in a reduced cross-sectional lens diameter and increased lens thickness, preferably on the order to 1 to 3 mm.

An alternative deforming method includes elongating or stretching the lens using tensile forces. Tweezers, forceps or other clamping tools can be utilized for this purpose wherein the lens is grasped at diametrically opposed positions about its periphery and stretched into an elongated, lozenge shape having an appropriately reduced cross-sectional diameter. Alternative deforming methods include rolling or folding the lenses to reduce their cross-sectional profiles. Exemplary methods for rolling or folding include those used to roll and fold elastomeric lenses such as those formed of silicones, as known in the art.

In order to deform the dehydrated lenses of the present invention without cracking or otherwise damaging the lens, the deforming step is performed at a temperature at which the dehydrated lens is sufficiently elastic for non-destructive deformation. More particularly, articles prepared from xerogel polymers can be deformed and reduced in size to a deformed configuration without damage when the deforming step is performed at temperatures which exceed the elastic deformation temperature of the polymer used. For many polymers, the elastic deformation temperature is in the same temperature region as the polymer's glass transition temperature, the temperature at which the polymer transforms from a glassy state to an elastic state. For purposes of the present invention, however, the deformation temperature and glass transition temperature can be separate thermodynamic temperatures. Within the temperature region between the deformation temperature and the polymer's degradation temperature, the polymer can be deformed through the controlled application of external force. However, if the external force is removed, the polymer will elastically return to its original configuration unless treated in accordance with the teachings of the present invention.

Those skilled in the art will appreciate that glass transition temperatures and polymer deformation temperatures vary from polymer to polymer. Typically, polymers increase in elasticity as the temperature increases above their glass transition temperatures. Accordingly, as discussed below, suitable elastic deformation temperatures should be separately determined for each type of hydrogel forming polymer used in the practice of the present invention. Preferably, the elastic deformation temperature is above ambient temperatures and, more preferably, above about 55° C. Those skilled in the art will appreciate that elastic deformation temperatures which are above the range of about 55° C. allow deformed articles which are exposed to elevated temperatures during shipping and storage to maintain their deformed configuration under ambient conditions. This is because the deformed article is subjected to temperatures below those temperatures which cause the deformed article to become elastic.

In accordance with the present invention, allowing the deformed dehydrated intraocular lens to cool to a suitable temperature below its elastic deforming temperature prior to removing the compression or elongation forces effectively freezes the deformed intraocular lens in its deformed configuration. At this lower freezing temperature the dehydrated intraocular lens does not require application of external forces to remain in the deformed configuration. In fact, once cooled below the elastic deformation or freezing temperature, the deformed articles remain deformed until exposed to conditions under which the polymer is again elastic, at which point the articles return to their original shapes.

Typically, a suitable freezing temperature is a temperature below the glass transition temperature of the hydrogel forming polymer in its xerogel form. At the lower temperature the polymer is in its plastic form as opposed to its higher temperature elastic form. In this plastic form the article is more pliable with little resilience. This contrasts with the elastic form where the deformed article returns to its original shape once the deformation forces are removed.

For purposes of practicing the present invention, and as mentioned above, preferred temperatures for freezing the deformed intraocular lenses in their deformed configuration are in the range of ambient temperatures. Thus, allowing the heated deformed intraocular lens to cool below about 30° C. provides a deformed intraocular lens which is frozen in its deformed configuration. This allows the deformed expansile intraocular lenses of the present invention to retain their deformed configuration during storage and shipping without refrigeration or special considerations.

Intraocular lenses and the hydrogel forming polymers utilized to form the lenses should meet certain physical characteristics so that the lenses are not damaged during the deforming processes of the present invention. The polymer xerogels or dehydrated forms should have sufficient elasticity at their deforming temperatures to allow the lenses to be deformed to sufficiently reduced sizes without breaking or cracking. Preferably, the lens material is not elastic at ambient temperatures, thus allowing the deformed lenses to remain in a deformed configuration during storage and shipping. Additionally, suitable polymeric materials for practicing the present invention will hydrate and swell to form hydrogels having sufficient water to exhibit elastic characteristics and shape memory properties at body temperatures, thereby enabling the lenses to reform to sizes, shapes and configurations effective for their intended functions as intraocular lens implants.

Any of the polymers currently utilized to form hydrogel intraocular lenses are suitable hydrogel forming polymers for purposes of practicing the present invention. Thus, commercially available hydrogel intraocular lenses can be deformed according to the processes of the present invention and then implanted utilizing small incision methodologies. Additionally, many other hydrogel forming polymers and copolymers having properties appropriate for fabricating hydrogel lenses are suitable hydrogel forming polymers for practicing the present invention.

Generally, hydrogel forming polymers are crosslinked polymers of water soluble or hydrophilic monomers or copolymers of water soluble and water insoluble monomers. Because of their importance in the field of biomaterial and agriculture, hydrogels and processes for their formation are well documented in the literature. Typical hydrogel materials include homopolymers and copolymers of acrylamides, methacrylamide, acrylate and methacrylate esters having at least one hydroxyl group on the side chain, such as 2-hydroxyethyl methacrylate, hydroxyethoxyethyl methacrylate, hydroxydiethoxy methacrylate, 2,3 dihydroxypropyl methacrylate, and glycerol methacrylate. Other suitable hydrogel forming polymers include polymers and copolymers of monomers such as methoxyethylethoxyethyl methacrylate, methoxydiethoxyethyl methacrylate, methoxyethyl methacrylate, methacrylate acid, vinyl alcohol, vinyl acetate, N-vinyl-2-pyrrolidone and related N-alkenyl-2-pyrrolidones, N-vinyl carbazole, N-vinyl succinimide, N-(- 3-picolyl) methacrylamide, N-vinylimidazole, and vinylpyridine.

In accordance with the present invention, a preferred exemplary hydrogel forming polymer is poly(N-vinyl pyrrolidone) polymerized with 2 wt % to 2.5 wt % tetraethyleneglycoldiacrylate. Additional exemplary hydrogel forming polymers are poly-2,3-dihyhdroxypropyl methacrylate, copolymers of N-vinyl pyrrolidone and 2-hydroxyethyl methacrylate, copolymers of N-vinyl pyrrolidone and N-vinylcarbazole, copolymers of N-vinyl succinimide, copolymers of N-vinylpyrrolidone and N-(-3-picolyl)methacrylamide, and copolymers of N-vinyl pyrrolidone and 4-vinylpyridine.

The hydrogels utilized to form intraocular lenses of the present invention may also include from about 0.1 wt % to about 10 wt % ultraviolet (UV) radiation absorbing compounds. Preferably, the UV absorbing compound is copolymerizable with the monomer forming the hydrogel polymer, thus becoming part of the final polymer or copolymer. This feature assures that the hydrated hydrogel is optically clear, and assures that the UV absorbing compound does not leach or migrate from an implanted lens.

As noted above, hydrogel materials may not be suitable for forming intraocular lens haptics in traditional radial filament configurations due to their flexibility. Accordingly, while it is contemplated as being within the scope of the present invention to utilize lenses having conventionally shaped haptics, it is preferred that the haptics be configured to account for the physical and structural properties of the hydrogel materials. Thus, as illustrated in FIG. 1, an exemplary lens configuration suitable for practicing the present invention is a bi-convex disc shaped lens, generally indicated by reference 10. Exemplary lens 10 is shown in its dehydrated state having dimensional characteristics sufficiently reduced from that of its intended, post-implantation hydrated configuration. Thus, the outer circumferential periphery 14 of the lens 10 is intended to position lens 10 within the capsular bag of the eye following implantation and hydration. Those skilled in the art will appreciate that periphery 14 can be provided with radially extending flanges or blade type haptics (not shown) if desired. In such a configuration, lens 10 would function as the optic portion of an intraocular lens having a larger overall diameter. Thus, full size hydrogel intraocular lens implants having optic diameters of up to 10 mm and overall diameters of up to 13 mm or more can be produced utilizing the techniques of the present invention so that these lenses can be effectively reduced in size and implanted utilizing small incision surgical techniques.

Figure 1B:
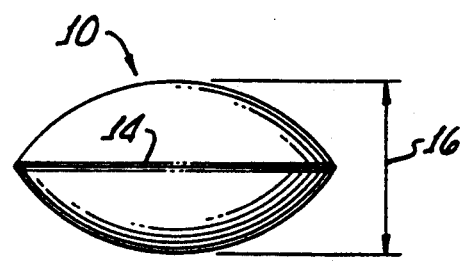
Figure 2A:
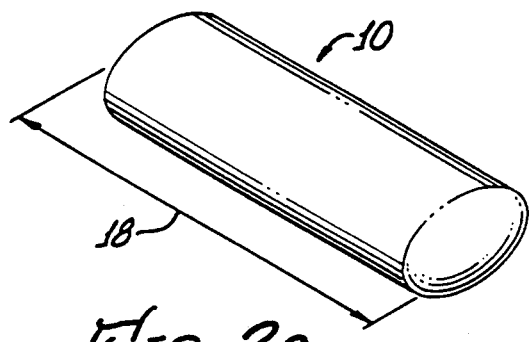
FIGS. 2a and b, respectively, illustrate an isometric view and an associated cross-sectional view of the exemplary small incision, full sized bi-convex, disc shape expansile hydrogel intraocular lens of FIG. 1 following deformation in accordance with the teachings of the present invention.
Figure 2B:
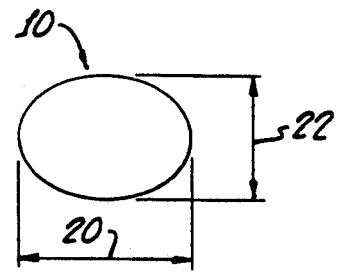
Figure 3A:
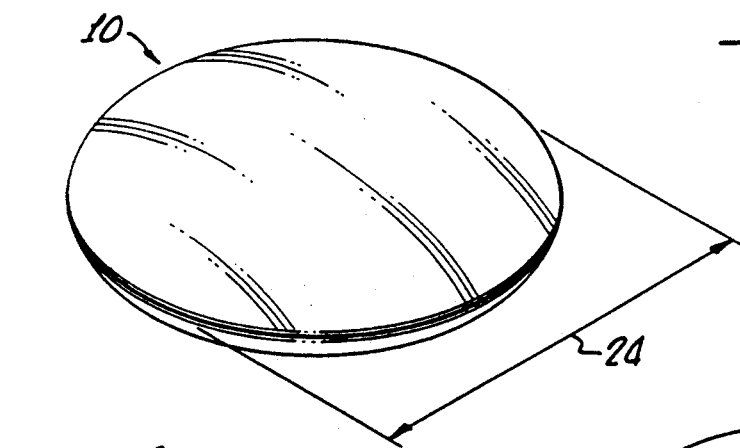
FIGS. 3a and b, respectively, illustrate an isometric view and an associated cross-sectional view of the exemplary small incision, full sized bi-convex, disc shape expansile hydrogel intraocular lens of FIGS. 1 and 2 following hydration and swelling reformation into its full sized post-implantation configuration.

More particularly, FIGS. 1-3 illustrate exemplary lens configurations suitable for practicing the fabrication and deformation methods of the present invention. FIGS. 1a and b illustrate the configuration of exemplary lens 10 in its dehydrated, reduced dimension form. FIGS. 2a and b illustrate an exemplary deformed configuration of lens 10 having at least one dimension sufficiently small to enable the lens to be inserted through a typical small incision lens implantation procedure. FIGS. 3a and b illustrate the post-implantation hydrated dimensions and configurations of lens 10.

In FIG. 1a lens 10 is shown as a circular, bi-convex lens in its dehydrated configuration having an exemplary diameter 12 ranging from approximately 4 to 7 mm. As shown in FIG. 1b an exemplary cross-sectional thickness 16 for lens 10 ranges from approximately 2 to 4 mm.

In accordance with the teachings of the present invention, lens 10 may be deformed in its dehydrated state into an elongated configuration as illustrated in FIG. 2a. Thus, by warming dehydrated lens 10 above its elastic deformation temperature, grasping opposite edges of circumferential periphery 14 with suitable tools and pulling, lens 10 may be pulled into the lozenge shape of FIG. 2a having a long dimension 18 on the order of 8 to 10 mm and, as illustrated in FIG. 2b, a cross-sectional width 20 of approximately 2 to 4 mm and a cross-sectional height 22 of approximate 2 to 3 mm. As noted above, the lozenge shape illustrated in FIG. 2a can also be produced by applying compressive forces across diameter 12 or through rolling and folding. Regardless of the deformation technique, before the deforming forces are removed lens 10 is allowed cool below its elastic deformation temperature to its freezing temperature. This can be accomplished by placing lens 10 in an appropriately configured fixture such as a tubular holder and allowing the heated lens to cool prior to removal from the holder or clamps.

As is readily apparent from FIGS. 2a and b, in its deformed configuration lens 10 can be inserted through an ocular incision on the order of 3 to 4 mm in length by presenting the reduced cross-sectional dimensions of the elongated, deformed lens and sliding the lens through the incision. Coating lens 10 with a viscoelastic material may facilitate this movement through the ocular incision. Advantageously, the deformed lens 10 illustrated in FIG. 2a and b is capable of minimizing the possibility of decentration once it is inserted in the ocular capsular bag. The ocular capsular bag has a general oval shape and the average size of the natural human lens is about 9.6 mm ×4.3 mm. The elongated shape of deformed lens 10 causes the lens to orient itself within the bag in alignment with the shape of the capsular bag. Additionally, the length of the elongated dimension acts as an anchor to secure the expansile deformed lens within the ocular capsular bag during the hydration process.

Figure 3B:
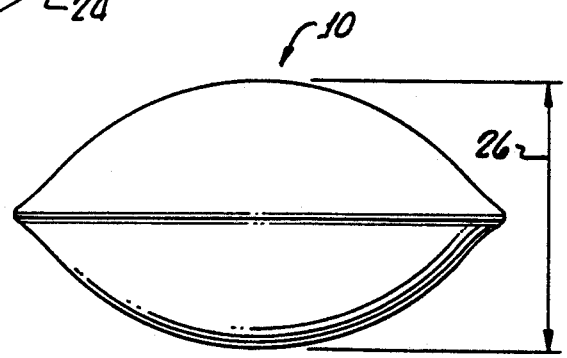

Following implantation lens 10 is allowed to hydrate and swell to an enlarged, full sized configuration as illustrated in FIGS. 3a and b. As shown in FIG. 3a, hydrated lens 10 has returned to its circular configuration and has enlarged to an expanded diameter 24 on the order of 8 to 10 mm. Similarly, as shown in FIG. 3b, the expanded cross-sectional thickness 26 of hydrated lens 10 is significantly larger than that of dehydrated cross-sectional thickness 16 and ranges on the order of 4 to 5 mm in this exemplary embodiment.

Thus, FIGS. 1-3 clearly demonstrate the dramatic reduction in at least one dimension of an expansile hydrogel lens that may be produced through the method of the present invention to provide a lens implant that can be inserted through a small incision surgical technique, yet will expand to a full size hydrated implant that reforms to its original configuration. By artfully combining the elasticity of the dehydrated lenses at elevated temperatures with their elastic memory behavior following hydration in combination with their swelling characteristics, the present invention provides full sized expansile hydrogel lenses that can be inserted through small surgical incisions.

It is also an aspect of the present invention to provide associated processes for surgically implanting such small incision intraocular lenses. An exemplary implantation process includes the steps of providing an ocular incision of less than about 4 mm in length and inserting such a deformed expansile intraocular lens through the ocular incision. Following insertion the deformed lens is allowed to hydrate and swell to an enlarged, full sized hydrogel intraocular lens having the configuration of the original reduced size lens only with enlarged dimensional characteristics.

Unlike prior art small incision procedures for implanting expansile intraocular lenses which are restricted to less than full sized hydrogel lenses, the processes of the present invention provide for the implantation of full sized hydrogel lenses. This is made possible because the processes of the present invention utilize both the hydration swelling and elastic memory characteristics of hydrogels. Moreover, the present invention contrasts with prior art methods for preparing deformed polymeric intraocular lenses for small incision implantation in that prior art processes depend upon only the temperature related elastic deformation properties of polymers. As mentioned above, the prior art deformation processes occur at physiological temperatures and elastic recovery occurs at physiological temperatures.

Thus, materials suitable for deforming according to prior art methods must have deformation temperatures which are close to physiological temperatures and freezing temperatures which are just below physiological temperatures. In any case, the maximum material deformation temperature is only slightly above 40° C. for these prior art processes. Generally, polymers having higher plasticizer content possess lower elastic deformation temperatures. Further, water incorporated in the polymer matrix of hydrogels acts as a plasticizer, effectively maintaining a low elastic deformation temperature compared with the xerogel state of the polymeric material. Typical hydrogels used to fabricate ophthalmic lenses have elastic deformation temperatures which are substantially below physiological temperatures. Accordingly, these hydrogels are not suitable for processing according to prior art deformation procedures since they do not remain deformed without external forces at room temperatures.

As mentioned above, in addition to being elastic at temperatures above the elastic deformation temperature, suitable hydrogel polymers for practicing the present invention are elastic in their hydrated form. Thus, by simply hydrating the deformed hydrogel intraocular lenses of the present invention, even at temperatures less than the elastic deformation temperature, the lenses return to an elastic state and recover their original configuration. This is in addition to the substantial size increase attributed to the hydrating and swelling action.

The following examples are offered as being illustrative of the principles of the present invention and not by way of limitation.

EXAMPLE 1

A total of ten different copolymers and homopolymers were prepared and evaluated for use as exemplary hydrogel forming materials of the present invention. Table I illustrates the proportions of each component of the polymerization mixture and presents comments relating to the polymer. Each polymerization procedure was carried out by first mixing the appropriate amounts of the monomer, comonomer, crosslinker and polymerization initiator as indicated in the first column of Table I. Then each mixture was transferred to an ampoule which was pre-treated with a silicone grease mold releasing agent. Each ampoule and mixture was then attached to a vacuum system and cooled with liquid nitrogen. After the mixture was frozen by the liquid nitrogen, the mixture was evacuated by turning on the vacuum system. Once a constant pressure was achieved, the vacuum system was turned off and the mixture was allowed to thaw by warming the ampoule in a water bath. This freeze-thaw cycle was repeated three times in order to provide sufficient mixture degassing. Finally, each mixture and ampoule were sealed under vacuum or an inert gas such as nitrogen or argon and polymerized. The polymerization temperatures and time periods varied with the particular monomers and comonomers in the polymerization mixture as indicated in the second column of Table I.

TABLE I

| MONOMERS AND COMPONENTS | POLYMERIZATION CONDITIONS | PROPERTIES | COMMENTS |
|---|---|---|---|
| (1) | | | |
| 7 ml DHPMA | 60° C./60h | Clear | Slow |
| 35 μl EGDMA | 110° C./24h | colorless | hydration |
| 7 mg AIBN | | solid; clear in swollen state | |
| (2) | | | |
| 7.96 ml NVP | 60° C./63h | Clear | Rapid |
| 40 μl TEGDA | 120° C./30h | colorless | hydration |
| 8 mg AIBN | | solid; clear in swollen state | |
| (3) | | | |
| 7.92 ml NVP | 60° C./63h | Clear | Rapid |
| 80 μl TEGDA | 120° C./30h | colorless | hydration |
| 8 mg AIBN | | solid; clear in swollen state | |
| (4) | | | |
| 9.8 ml NVP | 60° C./63h | Clear | Rapid |
| 0.2 ml TEGDA | 120° C./30h | colorless | hydration |
| 8 ml AIBN | | solid; clear in swollen state | IOLs made |
| (5) | | | |
| 3.96 g NVS | 50° C./48h | Clear | Low water |
| 40 mg TEGDA | 80° C./48h | colorless | content; |
| 4 mg AIBN | 100° C./6h | solid; clear in swollen state | intermediate hydration rate |
| (6) | | | |
| 5.54 g NVP | 50° C./48h | Clear | Intermediate |
| 1.39 g PIMA | 80° C./48h | colorless | hydration |
| 70 mg TEGDA | 120° C./6h | solid; clear in | rate |
| 7 mg AIBN | | | |

TABLE I-continued

| MONOMERS AND COMPONENTS | POLYMERIZATION CONDITIONS | PROPERTIES | COMMENTS |
|---|---|---|---|
| | | swollen state; water content 89% | rate |
| (7) 7.5 g NVP 7.5 g NVI 150 mg TEGDA 15 mg AIBN | 50° C./40h 80° C./96h | Clear slightly yellow solid; clear in swollen state; water content 94% | Rapid hydration |
| (8) 2.4 g NVI 0.6 g VP 60 μl TEGDA 3 mg AIBN | 60° C./48h 120° C./12h | Clear slightly yellow solid; clear in swollen state; water content 94% | Rapid hydration |
| (9) 7.5 g NVI 2.5 g VP 57 μl TEGDA 10 mg AIBN | 60° C./48h 120° C./24h | Clear slightly yellow solid; clear in swollen state; water content 94% | Rapid hydration |
| (10) 7.5 g NVI 2.5 g VP 100 μl TEGDA 10 mg AIBN | 60° C./48h 120° C./24h | Clear slightly yellow solid; clear in swollen state; water content 94% | Rapid hydration |

The abbreviations utilized in Table I are identified in Table II, immediately following.

TABLE II

| COMPONENTS | ABBREVIATION |
|---|---|
| 2,3-Dihydroxypropyl methacrylate | DHPMA |
| Ethylene glycol dimethacrylate | EGDMA |
| 2,2'-Azobisisobutyronitrile | AIBN |
| N-vinylpyrrolidone | NPV |
| Tetraethylene glycol diacrylate | TEGDA |
| N-vinylimidazole | NVI |
| N-(3-picolyl) methacrylamide | PIMA |
| 4-vinylpyridine | VP |
| N-vinylsuccinimide | NVS |

Figure 4:
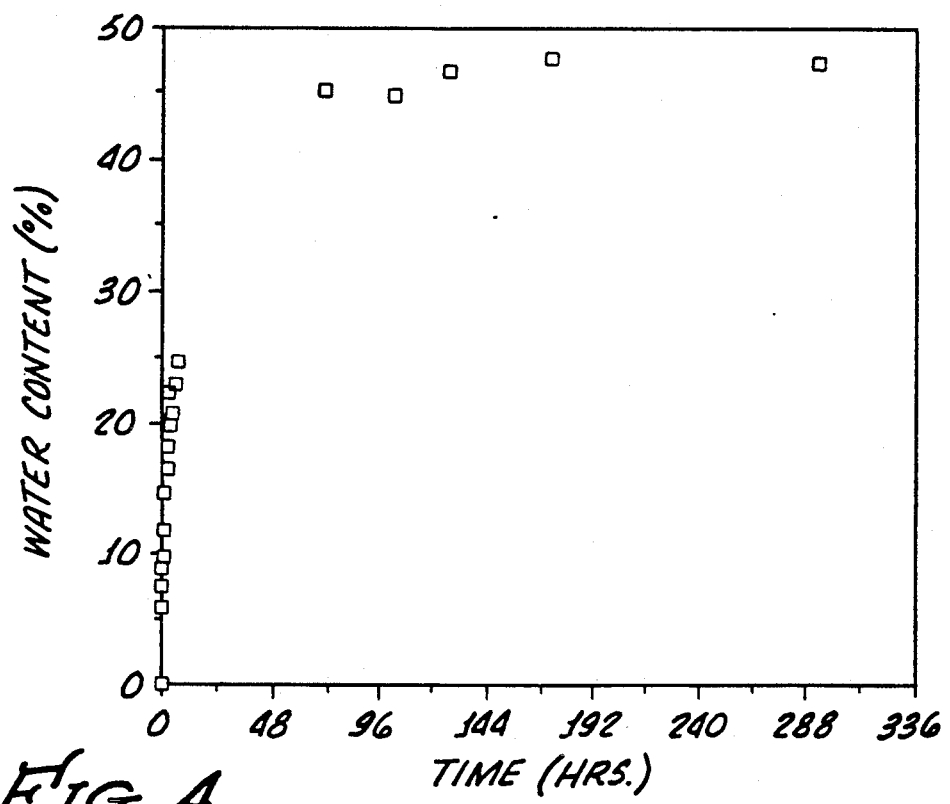
FIG. 4 is a graphical representation of the hydration characteristics of an exemplary DHPMA lens forming polymer illustrating the percent water up-take at room temperature over time and the equilibrium water content upon hydration.
Figure 5:
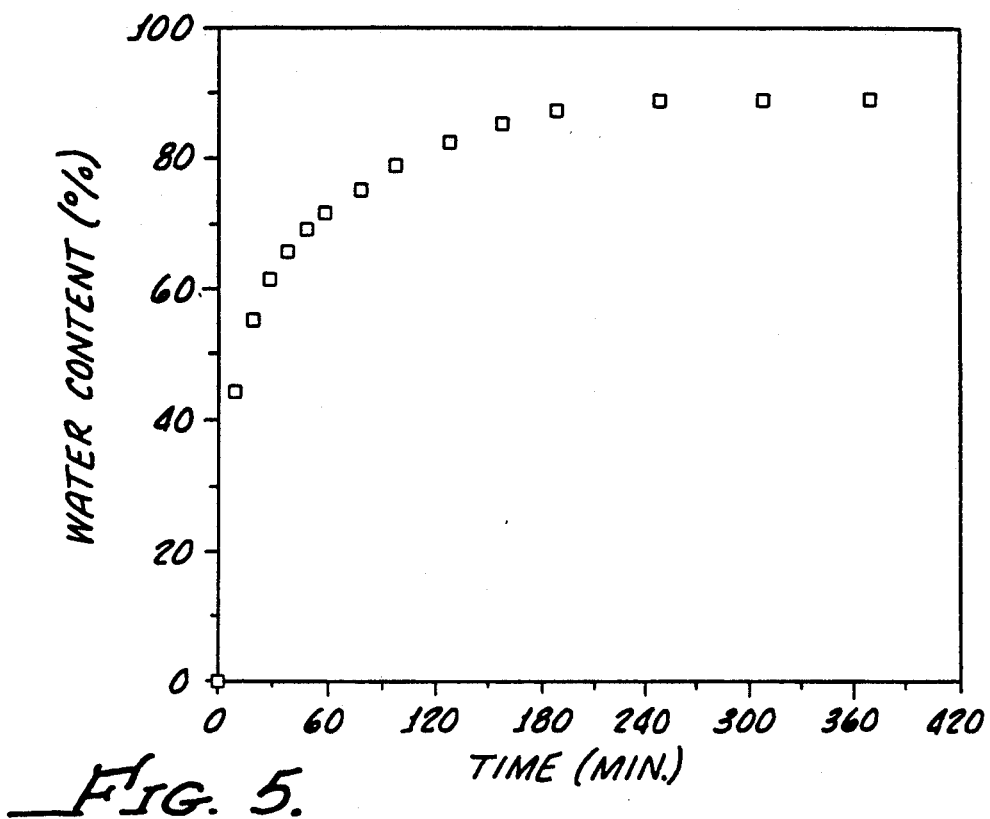
FIG. 5 is a graphical representation of the hydration characteristics of an exemplary TEGDA crosslinked NVP lens forming copolymer illustrating the percent water up-take at room temperature over time and the equilibrium water content upon hydration.
Figure 6:
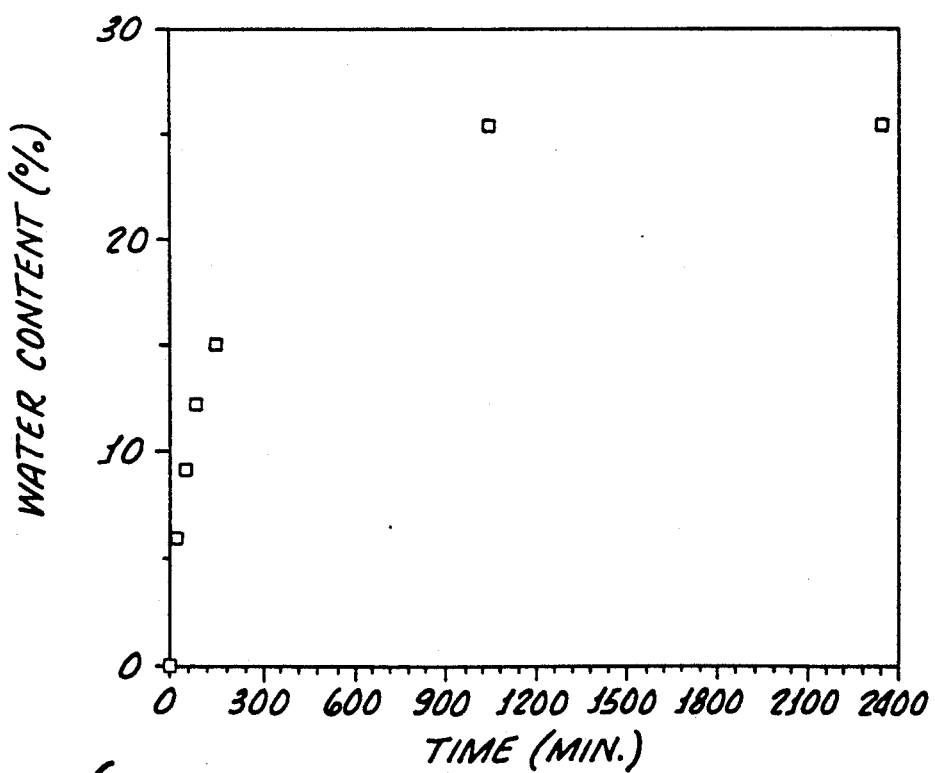
FIG. 6 is a graphical representation of the hydration characteristics of an exemplary crosslinked NVS lens forming copolymer illustrating the percent water up-take at room temperature over time and the equilibrium water content upon hydration.
Figure 7:
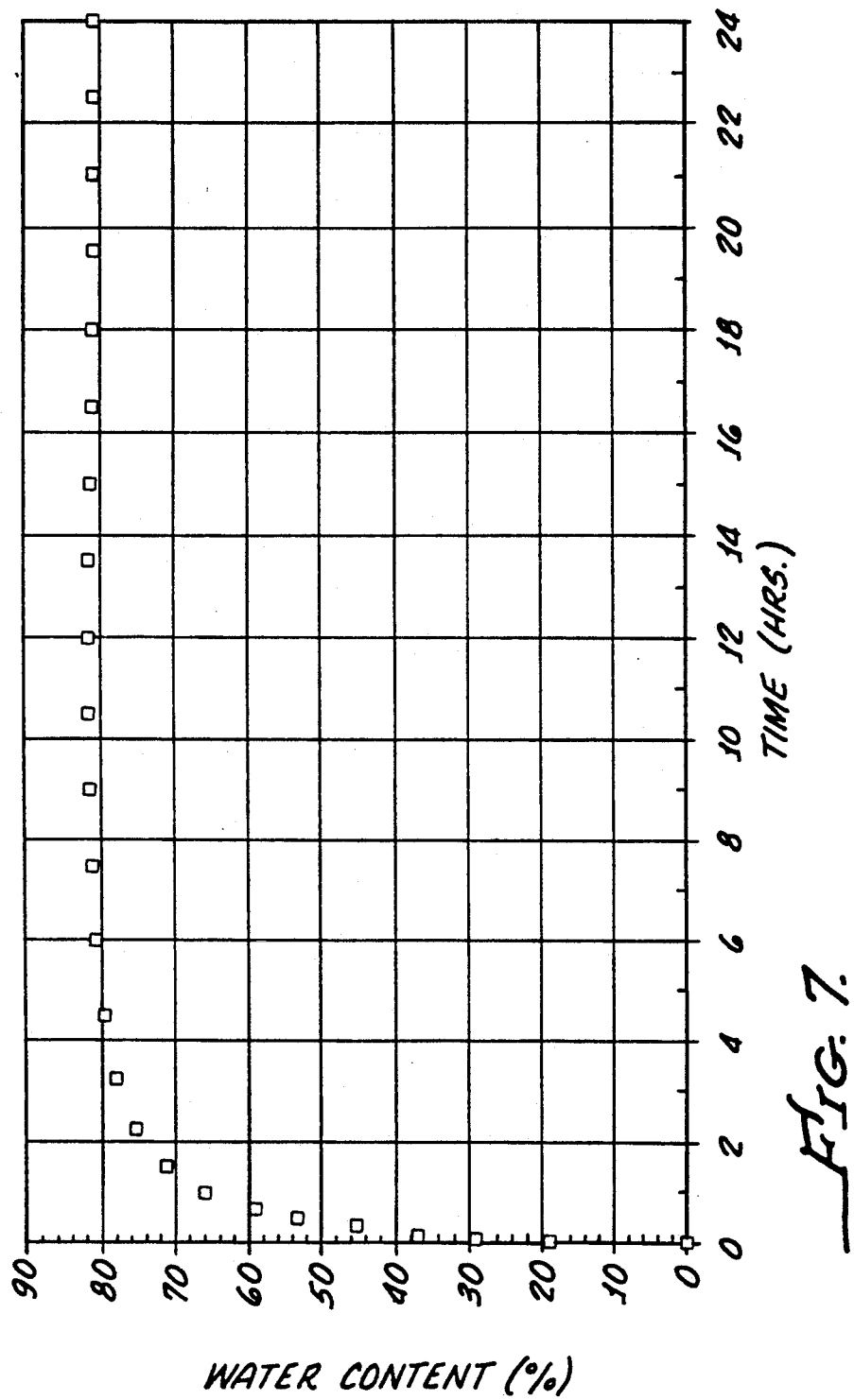
FIG. 7 is a graphical representation of the hydration characteristics of an exemplary NVP and PIMA lens forming copolymer illustrating the percent water up-take at room temperature over time and the equilibrium water content upon hydration.

The hydration characteristics and equilibrium water contents were determined for five of the polymers and copolymers identified in Table I. Water uptake profiles were determined by placing equal size blanks of each polymer or copolymer in deionized water and periodically weighing each sample to determine the weight increase caused by water uptake. These results were plotted to determine a water uptake profile and equilibrium hydration water content as illustrated in FIGS. 4 through 7. FIG. 4 illustrates the water uptake profile of an exemplary DHPMA polymer identified as polymer 1 in Table 1. Water content was measured over a period of 14 days of hydration and stabilized at an equilibrium water content of approximately 45% to 48% following 4 days of hydration. FIG. 5 illustrates a much faster water uptake profile of a TEGDA crosslinked NVP polymer identified as polymer 4 of Table I occurring over a 7 hour period. An equilibrium water content of approximately 85% was achieved in 6 hours. A 40 hour water uptake profile of crosslinked NVS polymer (polymer 5 of Table I) is illustrated in FIG. 6 and a 24 hour water uptake profile of a crosslinked polymer of NVP and PIMA (polymer 6 of Table I) is illustrated in FIG. 7.

EXAMPLE 2

In order to demonstrate the feasibility of the deformation method of the present invention a full sized expansile intraocular lens was prepared from polymer 4 of Table I by polymerizing a mixture of N-vinyl pyrrolidone and 2 wt % tetraethyleneglycol diacrylate with an AIBN initiator. The same general procedure described in Example 1 was utilized to prepare the mixture filled ampoule for polymerization and the polymerization process included a 72 hour cycle at 60° C. and a 48 hour cycle at 120° C. After the polymerized material was cooled the ampoule was broken open and the resulting polymer rod was cut into blanks. Each blank was then machined to an expansile intraocular lens in its dehydrated state. These blanks generally corresponded to the exemplary lens configuration 10 illustrated in FIGS. 1a and b. The machined dehydrated lenses had diameters 12 ranging from approximately 4.5 to 7.1 mm and cross-sectional thickness ranging from approximately 2.3 to 3.6 mm.

Exemplary lenses was deformed by heating a water bath to 60° C. and placing a beaker of heptane in the water bath. The lenses were immersed in the warm heptane for approximately 10 seconds and simultaneously folded with a pair of tweezers. The folded lenses were then removed from the heptane and inserted into 1/16 inch I.D. silicone tubes. The tube and folded lenses were then immersed in the warm heptane for 10-20 seconds. The tubes and lenses were removed from the heptane and immediately rolled and squeezed between two fingers, compressing the lenses into tightly folded and elongated shapes. The elongated lenses and tubes were allowed to cool to room temperature and then the lenses were removed from the tubes. At room temperature the lenses remained in their elongated state and had a configuration similar to that illustrated in FIGS. 2a and b. The long dimension 18 ranged from approximately 8 to 13 mm, the cross-sectional widths ranged from approximately 2 to 4 mm, and the cross-sectional heights ranged from approximately 1.8 to 3.0 mm.

Each lens was immersed in physiologically buffered aqueous solutions for 8-48 hours and allowed to hydrate to an equilibrium water content of about 85% by weight. The lenses were observed to expand and reform to the original configuration as illustrated in FIGS. 3a and b. The enlarged reconfigured hydrated lenses had expanded diameters 24 ranging from approximately 8.5 to 9.5 mm and expanded cross-sectional thicknesses 26 of approximately 4.5 mm.

EXAMPLE 3

Intra-ocular lenses were machined from lens blank formed of polymer 8 of Table I by polymerizing a mixture of N-vinyl imidazole, 4-vinyl pyridine (25 wt %), and tetraethyleneglycol diacrylate with an AIBN initiator. The same general procedure described in Example I was utilized to prepare the mixture filled ampoule for polymerization and the polymerization process also included a 48 hour cycle at 60° C. and a 24 hour cycle at 120° C.

Exemplary lenses were similar in dimensions to those described in Example 2. A typical optical resolution of the exemplary lenses in the dehydrated state was 80% as measured on a Meclab optical bench. The exemplary lenses were then deformed according to the procedures provided in Example 2. After hydration in physiologically buffered aqueous solutions for about 24 hours, the deformed lenses recovered their original configurations. As measured on a Meclab optical bench, a typical optical resolution of 70% was found for the hydrated lenses. This compares favorably with the 60% optical resolution minimally acceptable within the ophthalmic industry.

Having thus described exemplary embodiments of the present invention, it should be noted by those skilled in the art that the disclosures herein are exemplary only and that alternatives, adaptations and modifications may be made within the scope of the present invention.

I claim:

1. A process for fabricating expansile hydrogel intraocular lenses having reduced size for small incision insertion, said process comprising the steps of:

providing a dehydrate hydrogel intraocular lens formed of hydrogel forming polymer;

deforming said dehydrate hydrogel intraocular lens to provide a deformed dehydrated hydrogel intraocular lens sufficiently reduced in size to insert through a 4 mm surgical incision; and cooling said deformed dehydrated hydrogel intraocular lens to a temperature below said elastic deformation temperature of said hydrogel forming polymer, thereby freezing said deformed dehydrated intraocular lens at its reduced size, said deformed dehydrated hydrogel intraocular lens being capable of hydrating to a full size intraocular lens having an optical diameter of from about 6 mm to about 12 mm.

2. The process of claim 1 wherein said dehydrated hydrogel intraocular lens has an optical diameter of from about 3 mm to about 8 mm.

3. The process of claim 1 wherein said deformed dehydrated hydrogel intraocular lens is capable of hydrating to a full size intraocular lens having an optical diameter of from about 8 to about 10 mm.

4. The process of claim 1 wherein said hydrogel forming polymer is an ocular compatible material capable of having a hydrated water content of at least 20 wt %.

5. The process of claim 4 wherein said hydrogel forming polymer is prepared from one or more monomers selected from the group consisting of acrylamides, methacrylamides, water soluble vinyl monomers, acrylate and methacrylate esters having at least one hydroxyl group on a side chain.

6. The process of claim 4 wherein said hydrogel forming polymer is prepared from one or more monomers selected from the group consisting of 2-hydroxyethyl methacrylate, ethylene glycol dimethacrylate, hydroxyethoxyethyl methacrylate, hydroxydiethoxy methacrylate, 2,3 dihydroxypropyl methacrylate, glycerol methacrylate, methoxyethylethoxyethyl methacrylate, methoxydiethoxyethyl methacrylate, methoxyethyl methacrylate, methacrylate acid, vinyl alcohol, vinyl acetate, N-vinyl 2-pyrrolidone, N-vinyl sucinimide, N-(3-picoyl) methacrylamide, N-vinylimidazole, and 4-vinylpyridine.

7. The process of claim 1 wherein the elastic deformation temperature of said hydrogel forming material is at least 55° C.

8. The process of claim 1 wherein said dehydrated hydrogel intraocular lens is deformed through compressive elongation into a lozenge configuration.

9. The process of claim 1 wherein the deforming step further comprises heating said dehydrated hydrogel intraocular lens to a temperature at least as high as the elastic deformation temperature of said hydrogel forming polymer.

10. A process for fabricating an expansile hydrogel intraocular lens having reduced size for small incision insertion, said process comprising the steps of:

providing a dehydrate hydrogel intraocular lens formed of hydrogel forming polymer;

deforming said dehydrate hydrogel intraocular lens at a temperature at least as high as the elastic deformation temperature of said hydrogel forming polymer to provide a deformed dehydrated hydrogel intraocular lens sufficiently reduced in size to insert through a 4 mm surgical incision; and cooling said deformed dehydrated hydrogel intraocular lens to a temperature sufficiently below said elastic deformation temperature to freeze said deformed dehydrated hydrogel intraocular lens at its reduced size, said deformed dehydrated hydrogel intraocular lens being capable of hydrating to a full size intraocular lens having an optical diameter of from about 6 mm to about 12 mm.

11. The process of claim 10 wherein said dehydrated hydrogel intraocular lens has an optical diameter of from about 3 mm to about 8 mm.

12. The process of claim 10 wherein said deformed dehydrated hydrogel intraocular lens is capable of hydrating to a full size intraocular lens having an optical diameter of from about 8 mm to about 10 mm.

13. The process of claim 10 wherein said dehydrated hydrogel intraocular lens is deformed through compressive elongation into a lozenge configuration.

14. The process of claim 10 wherein said dehydrated hydrogel intraocular lens is deformed by folding and compressing said dehydrated hydrogel intraocular lens to provide a deformed configuration in the form of a folded and elongated lens.

15. The process of claim 10 wherein said hydrogel forming polymer is crosslinked N-vinyl pyrrolidone polymer and said elastic deformation temperature is approximately 60° C.

* * * * *

REEXAMINATION CERTIFICATE (2889th)

United States Patent [19]

Wang et al.

[11] B1 5,316,704

[45] Certificate Issued May 21, 1996

[54] PROCESS FOR FABRICATING FULL SIZED EXPANSIBLE HYDROGEL INTRAOCULAR LENSES

[75] Inventors: Yading Wang, Arcadia; Stephen O. Zhou, Hacienda Heights; Thomas P. Richards, Los Angeles, all of Calif.

[73] Assignee: Kabi Pharmacia Ophthalmics Inc., Monrovia, Calif.

Reexamination Request:
No. 90/003,866, Jun. 5, 1995

Reexamination Certificate for:
Patent No.: 5,316,704
Issued: May 31, 1994
Appl. No.: 951,775
Filed: Sep. 28, 1992

[51] Int. Cl.⁶ ............................................. B29D 11/00
[52] U.S. Cl. ........................... 264/2.6; 264/1.7; 264/2.7
[58] Field of Search ........................ 264/1.7, 2.6, 2.7; 425/808

[56] References Cited

U.S. PATENT DOCUMENTS

| | | | |
|---|---|---|---|
| 3,361,858 | 1/1968 | Wichterle | 264/2.6 |
| 4,573,998 | 3/1986 | Mazzocco | 623/6 |
| 4,731,079 | 3/1988 | Stoy | 623/6 |
| 4,743,254 | 5/1988 | Davenport | 623/6 |
| 4,808,182 | 2/1989 | Barrett | 623/6 |
| 4,813,954 | 3/1989 | Siepser | 623/6 |
| 4,833,890 | 5/1989 | Kelman | 623/6 |
| 4,834,753 | 5/1989 | Sulc et al. | 623/6 |
| 4,911,714 | 3/1990 | Poley | 623/6 |
| 4,919,662 | 4/1990 | Knoll et al. | 623/6 |
| 4,936,850 | 6/1990 | Barrett | 623/6 |
| 4,993,936 | 2/1991 | Siepser | 425/408 |
| 4,997,442 | 3/1991 | Barrett | 623/6 |
| 5,147,394 | 9/1992 | Siepser et al. | 623/6 |
| 5,217,491 | 6/1993 | Vanderbilt | 264/1.7 |

*Primary Examiner*—Mathieu Vargot

[57] ABSTRACT

Expansile hydrogel intraocular lenses are heated above their elastic deformation temperatures and deformed into an elongated configuration having at least one reduced dimension suitable for insertion through a small surgical incision. The lenses are allowed to cool in this configuration and retain the deformed shape prior to surgical implantation. Following implantation the lenses hydrate into an enlarged elastic form reassuming the original lens configuration of full capsule size.

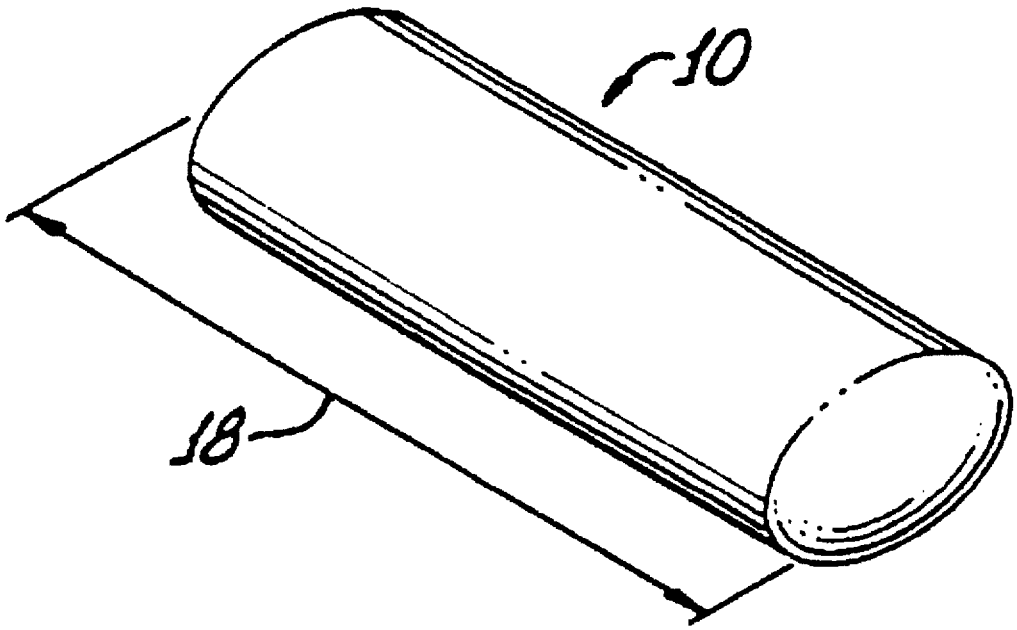

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *